United States Patent [19]
Rizzo

[11] 3,954,997
[45] May 4, 1976

[54] PESTICIDAL N-HYDROCARBYSULFENYL-N-ALKYL-N'-ARYLFORMAMIDINES

[75] Inventor: Victor L. Rizzo, Almena Township, Van Buren County, Mich.

[73] Assignee: The Upjohn Company, Kalamazoo, Mich.

[22] Filed: Dec. 30, 1974

[21] Appl. No.: 537,270

Related U.S. Application Data

[62] Division of Ser. No. 366,999, June 1, 1973, Pat. No. 3,887,619.

[52] U.S. Cl. ............................................. 424/326
[51] Int. Cl.² ........................................... A01N 9/20
[58] Field of Search ............... 424/326; 260/564 RF

[56] References Cited
OTHER PUBLICATIONS

Chemical Abstracts, 75:76431k (1971).
Chemical Abstracts, 77:126259z (1972).

Primary Examiner—Leonard Schenkman
Attorney, Agent, or Firm—John J. Killinger; Roman Saliwanchik

[57] ABSTRACT

Novel pesticidal N-hydrocarbylsulfenyl derivatives of N-alkyl-N'-aryl formamidines are disclosed with novel compositions thereof and methods of their use in controlling invertebrate pests, particularly insects and acarina. Certain of the novel compounds are particularly effective miticides.

11 Claims, No Drawings

PESTICIDAL N-HYDROCARBYSULFENYL-N-ALKYL-N'-ARYL-FORMAMIDINES

CROSS REFERENCE TO RELATED APPLICATIONS

This application is a division of application Ser. No. 366,999, filed June 1, 1973, now U.S. Pat. No. 3,887,619.

BACKGROUND OF THE INVENTION

1. Field of the Invention.

The invention concerns novel N-hydrocarbylsulfenyl derivatives of N-alkyl-N'-aryl formamidines, pesticidal compositions thereof and their use in the control of invertebrate pest populations.

2. Description of the Prior Art.

A number of N-alkyl-N'-aryl formamidines have been previously described as pesticides; see for example Belgian Pat. Nos. 760,141; 770,825 and German Pat. Nos. 1,172,081; 2,202,034.

The N-hydrocarbylsulfenyl derivatives of my invention are particularly advantageous commercially as invertebrate pesticides. For example, they are relatively stable both in storage and upon application in the field thus providing a long-lasting residual effectiveness.

In addition to killing invertebrate pests on contact, the compounds of the invention are absorbed by the vascular system of many plants, for example by cotton plants, and act systemically to kill the adult pests feeding upon the plant. Thus their period of pesticidal activity is further extended and non-feeding insects, i.e., insects not harmful to the plant are not unnecessarily killed during the whole period of pesticidal activity.

Compounds of the invention are also ovicidal, and are particularly effective in the control of acarine pest populations by this ovicidal action. Lepidopterous ova are also particularly susceptible to the compounds of the invention.

The compounds of the invention are also advantageous in that they exhibit relatively low mammalian toxicity and are non-phytotoxic at effective concentrations.

SUMMARY OF THE INVENTION

The invention comprises compounds selected from those of the formula:

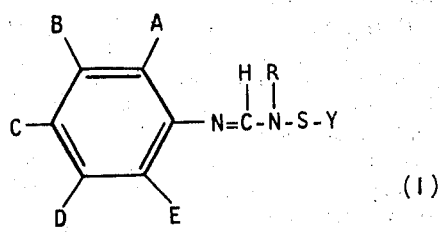

(I)

and the acid addition salts thereof wherein A is a group selected from halogen, lower alkyl, halogen-substituted lower alkyl, lower alkoxy and lower thioalkyl; B, C, D and E are each selected from hydrogen and a group A as defined above; R represents lower alkyl and Y is selected from hydrocarbyl, halogen-substituted hydrocarbyl, lower alkyl-substituted phenyl and lower alkoxy-substituted phenyl.

The term "hydrocarbyl" is used in the specification and claims as meaning the monovalent radical obtained by removing one hydrogen atom from the parent hydrocarbon, which latter contains 1 to 10 carbon atoms, inclusive. Illustrative of such hydrocarbyl groups are alkyl of 1 to 10 carbon atoms, inclusive, such as methyl, ethyl, propyl, butyl, pentyl, hexyl, heptyl, octyl, nonyl, decyl, and isomeric forms thereof; alkenyl of 2 to 10 carbon atoms, inclusive, such as vinyl, allyl, butenyl, pentenyl, hexenyl, heptenyl, octenyl, nonenyl, decenyl, and isomeric forms thereof; aryl of 6 to 10 carbon atoms, inclusive, such as phenyl, tolyl, xylyl, ethylphenyl, isopropylphenyl, naphthyl and the like; cycloalkyl of 5 to 10 carbon atoms, inclusive, such as cyclopentyl, cyclohexyl, methylcyclohexyl, ethylcyclohexyl, propylcyclohexyl, butylcyclohexyl and the like; and aralkyl of 7 to 10 carbon atoms, inclusive, such as benzyl, phenethyl, phenpropyl, phenbutyl and the like.

The term "halogen" is used herein in its conventional sense as embracive of chlorine, bromine, iodine and fluorine. The term "halo" means chloro, bromo, iodo and fluoro, respectively.

The term "halogen-substituted hydrocarbyl" is used herein to mean hydrocarbyl as defined above wherein one or more hydrogen atoms have been replaced with a halogen atom. Illustrative of halogen-substituted hydrocarbyl are chloromethyl, dichloromethyl, trichloromethyl, 1,2-dibromoethyl, 1,2-diiodobutyl, 1,1,2,2-tetrachloroethyl, trifluoromethyl, 1,1,2,2,3,3-hexafluorodecyl, 1,2-dibromoallyl, 1,1,1-trichloro-2-butenyl, chlorophenyl, bromotolyl, chlorocyclohexyl, iodobenzyl and the like.

The term "lower alkyl" is employed herein to mean alkyl as defined above, having 1 to 4 carbon atoms, inclusive. The term "halogen-substituted lower alkyl" means lower alkyl as defined above wherein 1 or more hydrogen atoms have been replaced by a halogen atom, as illustrated above.

The term "lower alkoxy" means the monovalent moiety of formula:

wherein lower alkyl is as defined above. Illustrative of lower alkoxy are methoxy, ethoxy, propoxy, butoxy and isomeric forms thereof.

The term "lower thioalkyl" is employed to mean thioalkyl of 1 to 4 carbon atoms, inclusive, such as for example thiomethyl, thioethyl, thiopropyl, thiobutyl and isomeric forms thereof.

The term "lower alkyl-substituted phenyl" means phenyl wherein a hydrogen atom has been replaced with a lower-alkyl group as previously defined.

The term "lower alkoxy-substituted phenyl is used throughout the specification and claims as meaning phenyl wherein a hydrogen atom has been replaced with a lower-alkoxy group as previously defined.

The invention also comprises invertebrate pesticidal compositions which comprise a pesticidally acceptable carrier and a pesticidally effective amount of a compound (I) of the invention. The compositions are useful in the method of the invention which is a process for controlling invertebrate pests, which comprises applying to a situs, effective amounts of the compounds (I) of the invention.

By the term "situs" I mean plants such as ornamentals, food crops, fruit trees, textile producing plants, berry bushes, lumber forests, farm yards, animal shelters, buildings, sanitary land-fill areas and like sites which are infected with or are potential infestation sites for invertebrate pests controllable with the compounds (I) of the invention.

The novel compounds (I) of the invention are useful in controlling invertebrate pest populations, i.e., in killing adults and ova of invertebrate pests or animals of the Phylum Arthropoda, for example those of Class Insecta such as those of the order Coleoptera as illustrated by the cotton boll weevil (*Anthonomus grandis* Bohenam); those of the order Lepidoptera as illustrated by the southern army worm (*Prodenia eridania* Cramer); those of Class Arachnida such as those of the order Acarina as illustrated by the 2-spotted spider mite (*Tetranychus telarius* Linnaeus or *Tetranychus urticae* Koch).

Compounds (I) of the invention having the specific formula:

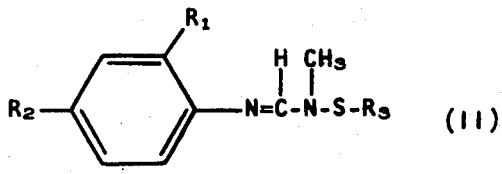

and their acid addition salts, wherein $R_1$ is lower alkyl, $R_2$ is selected from hydrogen, halogen and lower alkyl and $R_3$ is selected from lower alkyl, phenyl, halogen-substituted phenyl, lower alkyl-substituted phenyl, lower alkoxy-substituted phenyl and halogen-substituted lower alkyl; are preferred compounds of the invention for their acaricidal, i.e., miticidal activity, and their chemical stability.

Particularly preferred miticides of the invention are the Compounds (II) wherein $R_1$ and $R_2$ are each lower alkyl, preferably methyl and $R_3$ is selected from methyl, phenyl, halogen-substituted phenyl, methyl-substituted phenyl, and trichloromethyl.

DETAILED DESCRIPTION OF THE INVENTION

The compounds (I) of the invention are readily prepared by reacting together substantially equimolar proportions of N-alkyl-N'-phenyl formamidines (III) with sulfenyl chlorides (IV). The reaction which occurs is illustrated by the schematic formula:

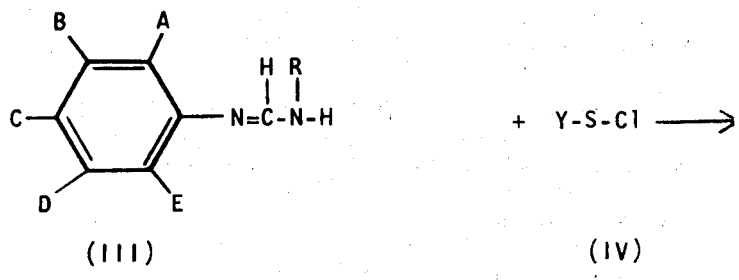

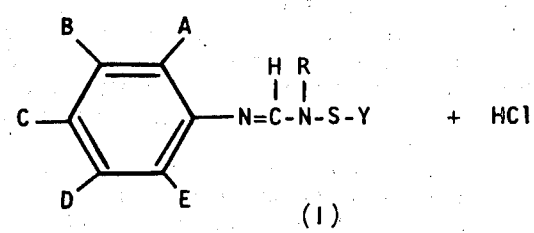

wherein A, B, C, D, E, R and Y have the meanings previously ascribed to them.

The above illustrated reaction is advantageously carried out in the presence of an inert organic solvent. An inert organic solvent is defined herein as a solvent for the formamidine reactant (III) which does not enter into reaction with the reaction mixture components or in any way alter the desired course of the reaction. Illustrative of inert organic solvents are tetrahydrofuran, benzene, diethylether, and methylene chloride. Preferred as the inert organic solvent is tetrahydrofuran.

The proportion of solvent employed is not critical, but advantageously is a sufficient quantity to solubilize the reactant formamidine (III).

During the course of the above illustrated reaction, hydrochloric acid is generated as a by-product. Preferably this acid is removed from the reaction mixture as it forms. This may be accomplished by conventional and known methods, for example by adding an acid acceptor compound to the reaction mixture. Examples of acid acceptor compounds are the tertiary amines such as trimethylamine, triethylamine, tripropylamine, tributylamine, pyridine and the like.

Although the above reaction may be carried out over a broad range of temperature conditions, i.e., from about −30° C. to about reflux temperature for the reaction mixture, it is preferably carried out at about 0° C.

Progress of the above reaction may be followed by conventional analytical methods, such as for example by nuclear magnetic resonance analysis which will show spectral characteristics of the product compounds (I) or by thin-layer chromatography which will show the appearance of product compounds (I). Upon completion of the reaction, the desired compounds (I) are readily separated from the reaction mixture by conventional methods such as by filtration to remove solid residues and distillation to remove solvents.

The formamidine reactants of formula (III) are generally well-known compounds as are methods of their preparation. In general, they may be prepared by condensing the appropriate aniline of formula:

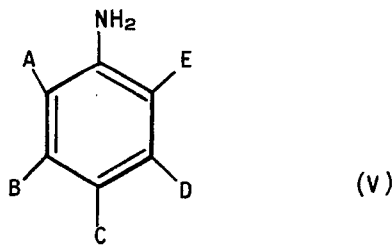

wherein A, B, C, D and E are as defined above with an appropriate formamide of formula:

wherein R is as previously defined. The condensation procedure is well known; see for example S. Africa Pat. No. 7,000,020, particularly Example 1. and Belgian Pat. No. 760,141 of June 10, 1971.

Aniline compounds (V) are well known, as illustrated by 2-methylaniline, 2-ethylaniline, 2-isopropylaniline, 2-n-butylaniline, 2-chloroaniline, 2-iodoaniline, 2-fluoroaniline, 2-trichloromethylaniline, 2-(bromomethyl)aniline, 2-methoxyaniline, 2-ethoxyaniline, 2-propoxyaniline, 2-butoxyaniline, 2-thiomethylaniline, 2-thioethylaniline, 2-thiopropylaniline, 2-thiobutylaniline, 2-chloro-3-methylaniline, 2-ethyl-3-methylaniline, 2-methyl-3-methoxyaniline, 2,3-dithiomethylaniline, 4-chloro-2-methylaniline, 2,4-dimethylaniline, 2,4-dimethoxyaniline, 2-ethyl-4-thioethylaniline, 2-methyl-4-trichloromethylaniline, 2,5-dimethylaniline, 2,5-dimethoxyaniline, 2,5-dibromoaniline, 2,5dithiobutylaniline, 2,6-dimethylaniline, 2-chloro-6-methoxyaniline, 2,6-dimethoxyaniline, 2,6-diiodoaniline, 2,6-ditrichloromethylaniline, 2,4,6-trichloroaniline, 2,4,6-trimethylaniline, 4-chloro-2,6-dimethylaniline, 4-ethoxy-2,6-trichloroaniline, 2,4,6-trithiomethylaniline and like anilines.

The formamide compounds (VI) are well known and are available commercially. Representative of the compounds (VI) are N-methylformamide, N-ethylformamide, and N-tertbutylformamide.

Sulfenyl halide reactants (IV) are also generally well known as is their preparation. Illustrative of the known alkanesulfenyl halides are methanesulfenyl chloride, ethanesulfenyl chloride, 1-propanesulfenyl chloride, 2-propanesulfenyl chloride, 1-n-butanesulfenyl chloride and trimethylmethanesulfenyl chloride. The higher alkanesulfenyl halides such as 1-hexanesulfenyl chloride and 1-decanesulfenyl chloride may be prepared by chlorination of the appropriate alkanedisulfides such as hexanedisulfide and decanedisulfide, respectively [see fro example Hubacker, Org. Syn. Coll., Vol. II, 455 (1943); Fuson et al., J. Org. Chem., 11, 469 (1946); Rheinboldt et al., Chem. Ber., 72, 657 and 668 (1939); and Douglass, Org. Sulfur Compounds, edited by Kharasch, Vol. I, Pergamon Press, N.Y. (1961), pg. 350]. The halo-substituted alkanesulfenyl halides are prepared by the same general procedure, and are illustrated by dichloromethanesulfenyl chloride, trichloromethanesulfenyl chloride, 2-chloroethanesulfenyl chloride, 1-chloropropane -2-sulfenyl chloride, trifluoromethanesulfenyl chloride and the like.

Cycloalkanesulfenyl halides within the formula IV, such as cyclohexanesulfenyl chloride and diethylcyclohexanesulfenyl chloride are also prepared by halogenation of the appropriate disulfide (Douglass, supra.).

Unsaturated aliphatic sulfenyl halides within the scope of formula (IV) are prepared by the same general method of Douglass, supra.; see for example U.S. Pat. Nos. 3,155,720; 3,489,766 and Barton et al., J. Org. Chem., 35, 1729 (1970). Illustrative of such compounds are 1,2-dichlorovinylsulfenyl chloride, 2,2-dichlorovinylsulfenyl chloride, 1-bromo-2-dichlorovinylsulfenyl chloride and trichlorovinylsulfenyl chloride.

Arylsulfenyl halides within the scope of the Formula IV such as benzenesulfenyl chloride, p-toluenesulfenyl chloride, 2-naphthalenesulfenyl chloride, p-chlorophenylsulfenyl chloride, 1-chloro-2-naphtahlenesulfenyl chloride and the like are well known as is the method of their preparation [see for example Kharasch et al., Chem. Rev., 39, 269 (1946)].

Aralkanesulfenyl halides within the scope of the formula (IV), may be prepared by the method of German Pat No. 804,572. Representative of such halides is the well-known α-toluenesulfenyl chloride.

Alkoxy-substituted benzenesulfenyl halides are conveniently prepared by the method of Montanari, Gazz. Chim. ital., 86, 406 (1956) and are illustrated by p-methoxyphenylsulfenyl chloride and the like.

The acid addition salts of the compounds (I) are prepared by reacting the free base (I) with a stoichiometric proportion of an appropriate acid such as hydrochloric acid. The method is well known to those skilled in the art, and may be carried out in aqueous or non-aqueous media such as ethanol, ether, ethyl acetate and the like. Illustrative of acid addition salts are those formed upon reacting a compound (I) of the invention with hydrobromic acid, sulfuric acid, phosphoric acid, acetic acid, lactic acid, citric acid, succinic acid, benzoic acid, salicylic acid and the like.

The acid addition salts are useful for the same purposes and in the same manner as the free base compounds (I) of the invention.

The pesticidal compounds (I) and their acid addition salts may be employed to control invertebrate pest populations, in their pure forms. However, it is preferred that they be applied to a situs in the form of a composition, comprising the compound (I) and a pesticidally acceptable diluent or carrier. Pesticidally acceptable carriers or diluents are well known in the art. For example, those compounds (I) which are solids at ambient temperatures may be formulated as granulars, dusts, wettable powders, emulsifiable concentrates, aqueous dispersions, solutions, and flowable creams for application to insects, mites, objects, or a situs. Those compounds (I) which are liquids at ambient temperatures may be formulated as emulsifiable concentrates, aqueous dispersions, suspensions, solutions, aerosols and the like.

Illustratively, dusts are readily formulated by grinding a mixture of the solid compounds (I) and a pulverulent carrier in the presence of each other. Grinding is conveniently accomplished in a ball mill, a hammer mill, or by air-blast micronization. A preferred ultimate particle size is less than 60 microns. Preferably, 95% of the particles are less than 50 microns, and about 75% are 5 to 20 microns. Dusts of that degree of comminution are conveniently free flowing and can be applied to inanimate matter, fruit trees, crop plants, and soil so as to effect thorough distribution and coverage. Dusts are particularly adapted for effectively controlling invertebrate pests such as insects and mites over wide areas when applied by airplane. They are also indicated for application to the undersides of plant foliage.

Representative pulverulent diluent carriers which are pesticidally acceptable are the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, sulfur, silica and silicates; chemically modified minerals such as washed bentonite, precipitated calcium silicate, synthetic magnesium silicate, and colloidal silica; and organic flours such as wood, walnut shell, soybean, cottonseed, and tobacco flours, and free-flowing hydrophobic starches.

Dusts may also be prepared by dissolving a compound (I) in a volatile solvent such as methylene chloride, mixing the solution with a pulverulent diluent carrier and evaporating the solvent.

The proportions of pulverulent carrier and compound (I) may be varied over a wide range depending upon the pests to be controlled and the conditions of treatment. In general, dust formulations contain up to about 50% (on a weight basis) of the compound (I) or a salt thereof as the active pesticide ingredient. Dusts having as little as 0.001% of the active ingredient may be used, but a generally preferred proportion is from about 0.50% to about 20% of the compound (I).

Dispersible powder formulations are prepared by incorporating a surfactant in a dust composition prepared as described above. By incorporating from 0.1% to about 12% of a surfactant in a dust, a dispersible powder is obtained which is particularly adapted for further admixture with water for spraying on inanimate matter and products, fruit trees, field crops, and soil. Such dispersible powders may be admixed with water to obtain any desired concentration of compound (I) and the mixture may be applied in amounts sufficient to obtain predetermined rates of application and uniform distribution. Preferably dispersible powders contain from about 10 percent to about 80 percent by weight of compound (I) as the active pesticide ingredient.

The surfactants employed may be characterized as capable of reducing the surface tension of water to less than about 40 dynes per centimeter in concentrations of about 1% or less.

Representative surfactants conventionally employed for preparing dispersible powder formulations include alkyl sulfates and sulfonates, alkyl aryl sulfonates, sulfosuccinate esters, polyoxyethylene sulfate, polyoxyethylenesorbitan monolaurate, alkyl-aryl polyether sulfates, alkyl-aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants for preparing compositions of this invention are blends of sulfonated oils and polyalcohol carboxylic acid esters such as the commercially available Emcol H-77, blends of polyoxyethylene ethers and oil-soluble sulfonates such as commercially available Emcol H-400, blends of alkyl aryl sulfonates and alkylphenoxy polyethoxy ethanols such as the commercially available Tritons X-151, X-161, and X-171, e.g., about equal parts of sodium dodecylbenzene-sulfonate and isooctylphenoxy polyethoxy ethanol containing about 12 ethoxy groups, and blends of calcium alkyl-aryl sulfonates and polyethoxylated vegetable oils such as commercially available Agrimul $N_4S$. The sulfate and sulfonate surfactants discussed above are preferably used in the form of their soluble salts, for example, their sodium salts.

If desired, dispersants such as methyl cellulose, polyvinyl alcohol, sodium ligninsulfonates, and the like may be included in the dispersible powder compositions of this invention. Adhesive or sticking agents such as vegetable oils, naturally occurring gums, casein, and others may also be included. Corrosion inhibitors such as epichlorohydrin and anti-foaming agents such as stearic acid may also be added if desired.

Granular compositions of this invention are convenient for application to soil when persistence is desired. Such compositions are readily applied by broadcast or by localized, e.g., in-the-row applications. The individual granules may be any desired size from 30 to 60 mesh up to 20 to 40 mesh, or even larger. Granulars are prepared by dissolving the active compound in a solvent such as methylene chloride, xylene, or acetone and applying the solution to a quantity of a granulated absorbent carrier. Representative granulated absorbent carriers are ground corn cobs, ground walnut shells, ground peanut hulls, and the like. When desired, the impregnated granulated absorbent carrier may be coated with a coating that will preserve the integrity of the granular until it is applied to an object or situs favorable for release of the active ingredient. Such coatings are well known in the art.

The compounds (I) of the invention may also be admixed with other known pesticides to form compositions of the invention. For example, they may be mixed with malathion, azinphosmethyl, carbaryl, methoxychlor, and like pesticidal compounds.

The compounds (I) of the invention may be applied to insects, mites, objects, or a situs in aqueous sprays without a solid carrier. Such aqueous sprays are advantageous for certain types of spray equipment and conditions of application as is well known in the art. They are also advantageous when uniform dispersions, homogeneous solutions, or other easily mixed aqueous sprays are desired.

Aqueous sprays without a solid carrier are prepared from concentrated solutions of the compounds (I) of the invention in an inert organic solvent carrier. The inert organic solvent carrier may be one that is miscible or immiscible with water. The compounds (I) that are somewhat soluble in water may be dissolved in a water miscible solvent carrier, e.g., ethanol and mixed with water to give homogeneous solutions. The compounds (I) that are less soluble in water may be dissolved in a solvent carrier that is immiscible with water and the solution dispersed in water to give a uniform dispersion, e.g., an emulsion.

In an oil-in-water emulsion, the solvent phase is dispersed in the water phase and the dispersed phase contains the compound (I). In this way, uniform distribution of a water insoluble compound (I) is achieved in an aqueous spray. A solvent carrier in which the compounds (I) are highly soluble is desirable so that relatively high concentrations of the compound (I) can be obtained. One or more solvent carriers with or without a co-solvent may be used in order to obtain concentrated solutions of the compounds (I), the main consideration being to employ a water-immiscible solvent for the compound (I) that will hold the compound in solution over the range of concentrations useful for applying to invertebrate pests or a situs.

The emulsifiable concentrate compositions of the invention are preferred compositions prepared by dissolving the compound (I) as the active ingredient and a surfactant such as one of those previously described, in a substantially water-immiscible solvent carrier (i.e., a solvent carrier which is soluble in water to the extent of less than 2.5% by volume at temperatures of the order of 20° C. to 30° C.), for example, cyclohexanone, methyl propyl ketone, summer oils (a paraffinic, intermediate distillation fraction having a viscosity range from 40 to 85 seconds Saybolt and an unsulfonatable residue over 90 percent), ethylene dichloride; aromatic hydrocarbons such as benzene, toluene, and xylene, and high-boiling petroleum hydrocarbons such as kerosene, diesel oil, and the like. When desired, a co-solvent such as methyl ethyl ketone, acetone, isopropanol, and the like may be included with the solvent carrier in order to enhance the solubility of the compound (I). Aqueous emulsions are prepared by mixing the concentrate with water to give any desired concentration of compounds (I).

Advantageously, the concentration of compound (I) in emulsifiable concentrates will range from about 5 percent to about 50 percent by weight, preferably from about 10 percent to about 40 percent. A concentrate comprising 20 percent by weight of the compound (I) dissolved in a water-immiscible solvent of the kind noted above may be admixed with an aqueous medium in the proportions of 13 ml. of concentrate with 1 gal. of medium to give a mixture containing 700 parts of compounds (I) per million parts of liquid carrier. Similarly, 1 qt. of a 20 percent concentrate mixed with 40 gals. of water provides about 1200 ppm (parts per million) of a compound (I). In the same manner, more concentrated solutions of active ingredient may be prepared by adjusting upward the proportion of compound (I) or the acid addition salt thereof.

The above described concentrate compositions of the invention which are intended for use in the form of aqueous dispersions or emulsions may also contain advantageously a humectant, i.e., an agent which will delay the drying of the composition in contact with material to which it has been applied. Conventionally used humectants are exemplified by glycerol, diethylene glycol, solubilized lignins, such as calcium ligninsulfonate, and the like.

For use in an aerosol, the compound (I) or its acid addition salt may be dissolved in acetone or a mixture of acetone and a heavy petroleum oil and mixed in a thick-walled canister or bomb with a propellant such as methyl chloride or dichlorodifluoromethane.

The compositions containing compounds (I) of the invention or their acid addition salts may be applied to invertebrate pests or pestiferous sites by conventional methods. For example, an area of soil, a building, or plants may be treated by spraying wettable powder suspensions, emulsions, or solutions from powder sprayers or from hand-operated knapsack sprayers. Dusts can be applied by power dusters, or by hand-operated dusters. Creams and ointment formulations may be applied to objects for prolonged protection from insects and mites.

It will of course be appreciated by those skilled in the art that the conditions encountered when applying the method and compositions of this invention to actual practice can vary widely. Among the variables that may be encountered are the degree of infestation by pests, the particular pest to be controlled, the specific compound (I) employed, the particular situs being treated, the age or degree of development of plants to be protected, the prevailing weather conditions, such as temperature, relative humidity, rainfall, dews, and like environmental conditions. Dependent upon the variables encountered in a given situation, the amount of compounds (I) to be employed as an effective amount, the frequency of application and the technique of application will be adjusted for optimum effect, as those skilled in the art well appreciate.

In general, efficacy of the compounds (I) and their acid addition salts against invertebrate pests has been demonstrated at concentrations of 1000, 500, 100, 50 and even 30 ppm of the novel compounds (I) depending upon the specific pest to be killed. Some invertebrate animal pests will be more sensitive to the compounds (I) than others. Methods of testing a given compound (I) or its salt to determine the maximum effective concentration required for killing a specific invertebrate pest are well known; see for example U.S. Pat. Nos. 3,474,170; 3,476,836 and 3,478,029. In general, effective amounts of the compounds (I) or their acid addition salts for pesticidal activity is obtained when the compounds (I) or its salt are applied at concentrations of about 30 to about 6000 ppm, preferably at concentrations of about 100 to about 4000 ppm.

The following examples describe the manner and process of making and using the invention and set forth the best mode contemplated by the inventor of carrying out the invention but are not to be construed as limiting.

EXAMPLE 1

N-Methyl-N-(phenylthio-N'-2,4-xylyl formamidine

To 3.24 gms. (0.02 mole) of N-methyl-N'-2,4-xylyl formamidine (prepared by the method of Belgian Pat. No. 760,141) in 50 ml. of tetrahydrofuran there is added 2.02 gms. (0.02 mole) of triethylamine. The resulting mixture is cooled in an ice bath and 2.89 g. (0.02 mole) of benzenesulfenyl chloride is added with stirring. The resulting reaction mixture is then stirred at room temperature for ½ hour. The mixture is then filtered and the solvent stripped from the filtrate to yield 4.6 gms. (85.5% of theory) of N-methyl-N-(phenylthio)-N'-2,4-xylyl formamidine in the form of a colorless oil.

Analysis: Calc'd. for $C_{16}H_{18}N_2S$ (percent); C, 71.07; H, 6.71; N, 10.36. Found (percent); C, 71.13; H, 6.60; N, 10.09.

Similarly, following the above procedure but replacing the N-methyl-N'-2,4-xylyl formamidine as used therein with an equal molar proportion of each of N-ethyl-N'-2,4-xylyl formamidine;

N-ethyl-N'-(2-methyl-4-chlorophenyl) formamidine;
N-n-propyl-N'-2,4-xylyl formamidine;
N-n-propyl-N'-(2-methyl-4-chlorophenyl) formamidine;
N-isopropyl-N'-2,4-xylyl formamidine; and
N-isopropyl-N'-(2-methyl-4-chlorophenyl) formamidine;
respectively, all of which are prepared by reaction of the appropriate aniline of formula (V) with the appropriate formamide (VI) according to the method of Belgian Pat. No. 760,141; there is obtained N-ethyl-N-(phenylthio)-N'-2,4-xylyl formamidine;

N-ethyl-N-(phenylthio)-N'-(2-methyl-4-chlorophenyl) formamidine;

N-n-propyl-N-(phenylthio)-N'-2,4-xylyl formamidine;

N-n-propyl-N-(phenylthio)-N'-(2-methyl-4-chlorophenyl) formamidine;

N-isopropyl-N-(phenylthio)-N'-2,4-xylyl formamidine; and

N-isopropyl-N-(phenylthio)-N'-(2-methyl-4-chlorophenyl) formamidine, respectively.

EXAMPLE 2

N-Methyl-N-(phenylthio)-N'-(2-methyl-4-chlorophenyl) formamidine

To 3.66 gms. (0.02 mole) of N-methyl-N'-(2-methyl-4-chlorophenyl) formamidine (S. African Pat. No. 7,000,020) in 100 ml. tetrahydrofuran there is added 2.02 gms. (0.02 mole) of triethylamine. The mixture is cooled in an ice bath and 2.89 gms. (0.02 mole) of benzenesulfenyl chloride is added with stirring. The reaction mixture is then stirred at room temperature for ½ hour, filtered and the filtrate solvent stripped to yield 5.0 gms. (86.5% of theory) of N-methyl-N-(phenylthio)-N'-(2-methyl-4-chlorophenyl) formamidine in the form of a colorless oil.

Analysis: Calc'd. for $C_{15}H_{15}ClN_2S$ (percent); C, 61.95; H, 5.20; N, 9.63. Found (percent); C, 61.80; H, 5.04; N, 9.54.

EXAMPLE 3

N-Methyl-N-(4-methoxyphenylthio)-N'-2,4-xylyl formamidine

To 1.62 gms. (0.01 mole) of N-methyl-N'-2,4-xylyl formamidine in 50 ml. tetrahydrofuran there is added 1.01 gms. (0.01 mole) of triethylamine. The mixture is cooled in an ice bath and 1.75 gms. (0.01 mole) of p-methoxyphenylsulfenyl chloride is added with stirring. The reaction mixture is then stirred at room temperature for ½ hour, and the filtrate stripped of solvent to yield 2.7 gms. (90% of theory) of N-methyl-N-(4-methoxyphenylthio)-N'-2,4-xylyl formamidine in the form of a colorless oil.

Analysis: Calc'd. for $C_{17}H_{20}N_2OS$ (percent); C, 67.97; H, 6.71; N, 9.32. Found (percent); C, 67.61; H, 6.68; N, 9.26.

Similarly, following the above procedure but replacing the p-methoxyphenylsulfenyl chloride as used therein with an equal molar proportion of:

1. ethanesulfenyl chloride, there is obtained N-methyl-N-(ethylthio)-N'-2,4-xylyl formamidine;
2. propanesulfenyl chloride, there is obtained N-methyl-N-(propylthio)-N'-2,4-xylyl formamidine; and
3. butanesulfenyl chloride, there is obtained N-methyl-N-(butylthio)-N'-2,4-xylyl formamidine.

EXAMPLE 4

N-Methyl-N-(phenylthio)-N'-o-tolyl formamidine

To 2.96 gms. (0.02 mole) of N-methyl-N'-o-tolyl formamidine (prepared by reacting N-methylformamide with 2-methylaniline according to the method of Belgian Pat. No. 760,141) in 50 ml. tetrahydrofuran there is added 2.02 gms. (0.02 mole) of triethylamine. The mixture is then cooled in an ice bath and 2.89 gms. (0.02 mole) of benzenesulfenylchloride added with stirring. The reaction mixture is then stirred at room temperature for ½ hour, filtered and solvent stripped from the filtrate to yield 4.0 gms. (78% of theory) of N-methyl-N-(phenylthio)-N'-o-tolyl formamidine in the form of a light amber oil.

Analysis: Calc'd. for $C_{15}H_{16}N_2S$ (percent); C, 70.27; H, 6.29; N, 10.93. Found (percent); C, 69.47; H, 6.22; N, 10.68.

Similarly, repeating the above procedure but replacing the benzenesulfenyl chloride as used therein with an equal molar proportion of each of decanesulfenyl chloride (prepared by chlorination of decanedisulfide according to the method of Douglass, supra.), 1,2-dichlorovinylsulfenyl chloride, 2-naphthalenesulfenyl chloride, cyclohexanesulfenyl chloride (prepared by chlorination of cyclohexanedisulfide, according to the method of Douglass, supra.) and α-toluenesulfenyl chloride, respectively, there is obtained:

N-methyl-N-decylthio-N'-o-tolyl formamidine;

N-methyl-N-(1,2-dichlorovinylthio)-N'-o-tolyl formamidine;

N-methyl-N-(naphthylthio)-N'-o-tolyl formamidine;

N-methyl-N-(cyclohexylthio)-N'-o-tolyl formamidine; and

N-methyl-N-(benzylthio)-N'-o-tolyl formamidine, respectively.

Similarly, following the above procedure but replacing the benzenesulfenyl chloride as used therein with an equal molar proportion of ethanesulfenyl chloride and replacing the N-methyl-N'-o-tolyl formamidine as used therein with an equal molar proportion of N-ethyl-N'-2,4-xylyl formamidine;

N-ethyl-N'-(2-methyl-4-chlorophenyl) formamidine;

N-n-propyl-N'-2,4-xylyl formamidine;

N-n-propyl-N'-(2-methyl-4-chlorophenyl) formamidine;

N-isopropyl-N'-(2-methyl-4-chlorophenyl) formamidine; and

N-isopropyl-N'-2,4-xylyl formamidine, respectively, all of which are prepared by reaction of the appropriate aniline of formula (V) with an appropriate formamide of formula (VI) (method of Belgian Pat. No. 760,141); there is obtained N-ethyl-N-(ethylthio)-N'-2,4-xylyl formamidine;

N-ethyl-N-(ethylthio)-N'-(2-methyl-4-chlorophenyl) formamidine;

N-n-propyl-N-(ethylthio)-N'-2,4-xylyl formamidine;

N-n-propyl-N-(ethylthio)-N'-(2-methyl-4-chlorophenyl) formamidine;

N-isopropyl-N-(ethylthio)-N'-(2-methyl-4-chlorophenyl) formamidine; and

N-isopropyl-N-(ethylthio)-N'-2,4-xylyl formamidine, respectively.

EXAMPLE 5

N-Methyl-N-(4-methoxyphenylthio)-N'-(2-methyl-4-chlorophenyl) formamidine

To 1.82 gms. (0.01 mole) of N-methyl-N'-(2-methyl-4-chlorophenyl) formamidine (S. African Pat. No. 7,000,020) in 50 ml. tetrahydrofuran there is added 1.01 gms. (0.01 mole) of triethylamine. The mixture is cooled in an ice bath and 1.75 gms. (0.01 mole) of p-methoxyphenylsulfenyl chloride is added with stirring. The reaction mixture is stirred at room temperature for ½ hour, filtered and the filtrate stripped of solvent to yield 2.8 gms. (87.5% of theory) of N-methyl-N-(4-methoxyphenylthio)-N'-(2-methyl-4-chlorophenyl) formamidine in the form of a red oil.

Analysis: Calc'd. for $C_{16}H_{17}ClN_2OS$ (percent); C, 59.89; H, 5.34; N, 8.73. Found (percent); C, 58.67; H, 5.36; N, 8.37.

Similarly, following the above procedure but replacing the p-methoxysulfenyl chloride as used therein with an equal molar proportion of 1. ethanesulfenyl chloride, there is obtained N-methyl-N-(ethylthio)-N'-(2-methyl-4-chlorophenyl) formamidine;
2. n-propanesulfenyl chloride, there is obtained N-methyl-N-(propylthio)-N'-(2-methyl-4-chlorophenyl) formamidine;
3. isopropanesulfenyl chloride, there is obtained N-methyl-N-(isopropylthio)-N'-(2-methyl-4-chlorophenyl) formamidine; and
4. n-butanesulfenyl chloride, there is obtained N-methyl-N-(butylthio)-N'-(2-methyl-4-chlorophenyl) formamidine.

EXAMPLE 6

N-Methyl-N-(trichloromethylthio)-N'-2,4-xylyl formamidine

To 3.24 gms. (0.02 mole) of N-methyl-N'-2,4-xylyl formamidine in 50 ml. tetrahydrofuran there is added 2.02 gms. (0.02 mole) of triethylamine. The mixture is cooled in an ice bath and 3.71 gms. (0.02 mole) of trichloromethanesulfenyl chloride is added with stirring. The reaction mixture is then stirred at room temperature for ½ hour, filtered and the filtrate stripped of solvent to yield 6.0 gms. (96% of theory) of crude N-methyl-N-(trichloromethylthio)-N'-2,4-xylyl formamidine in the form of a red-orange colored oil. The oil may be purified if desired by chromatographic methods on silica gel, eluting with benzene-ethyl acetate 9:1.

Analysis: Calc'd. for $C_{11}H_{13}Cl_3N_2S$ (percent); C, 42.39; H, 4.20; Cl, 34.13; N, 8.99. Found (percent); C, 42.23; H, 4.27; Cl, 34.07; N, 9.21.

Similarly, following the above procedure but replacing the N-methyl-N'-2,4-xylyl formamidine as used therein with an equal molar proportion of N-ethyl-N'-2,4-xylyl formamidine; N-n-propyl-N'-2,4-xylyl formamidine; and N-isopropyl-N'-2,4-xylyl formamidine; respectively, all of which are prepared by reaction of the appropriate aniline (V) with an appropriate formamide (VI) by the method of Belgian Pat. No. 760,141; there is obtained N-ethyl-N-(trichloromethylthio)-N'-2,4-xylyl formamidine, N-n-propyl-N-(trichloromethylthio)-N'-2,4-xylyl formamidine and N-isopropyl-N-(trichloromethylthio)-N'-2,4-xylyl formamidine, respectively.

EXAMPLE 7

N-Methyl-N-(p-tolylthio)-N'-2,4-xylyl formamidine

To 1.62 gms. (0.01 mole) of N-methyl-N'-2,4-xylyl formamidine in 50 ml. tetrahydrofuran is added 1.01 gms. (0.01 mole) of triethylamine. The mixture is cooled in an ice bath and 1.6 gms. (0.01 mole) of p-toluenesulfenyl chloride is added with stirring. The reaction mixture is then stirred at room temperature for ½ hour, filtered and the filtrate stripped of solvent to yield 2.6 gms. (91.5% of theory) of N-methyl-N-(p-tolylthio)-N'-2,4-xylyl formamidine in the form of a colorless oil.

Analysis: Calc'd. for $C_{17}H_{20}N_2S$ (percent); C, 71.79; H, 7.09; N, 9.85. Found (percent); C, 72.26; H, 7.23; N, 10.24.

EXAMPLE 8

N-Methyl-N-(trichloromethylthio)-N'-(2-methyl-4-chlorophenyl) formamidine

To 5.48 gms. (0.03 mole) of N-methyl-N'-(2-methyl-4-chlorophenyl) formamidine in 100 ml. tetrahydrofuran is added 3.03 gms. (0.03 mole) of triethylamine. The mixture is cooled in an ice bath, and 5.58 gms. (0.03 mole) of trichloromethanesulfenyl chloride is added with stirring. The reaction mixture is then stirred at room temperature for ½ hour, filtered and the filtrate stripped of solvent to yield 8.5 gms. (85.0% of theory) of a yellow oil. The oil is chromatographed over 30 gms. of silica gel using benzene as the elutent to yield 7.0 gms. of N-methyl-N-(trichloromethylthio)-N'-(2-methyl-4-chlorophenyl) formamidine in the form of a yellow oil.

Analysis: Calc'd. for $C_{10}H_{10}Cl_4N_2S$ (percent); C, 36.17; H, 3.04; N, 8.43. Found (percent); C, 36.42; H, 3.00; N, 9.06.

Similarly, following the above procedure but replacing the N-methyl-N'-(2-methyl-4-chlorophenyl) formamidine as used therein with an equal molar proportion of N-ethyl-N'-(2-methyl-4-chlorophenyl) formamidine; N-n-propyl-N'-(2-methyl-4-chlorophenyl) formamidine; and N-isopropyl-N'-(2-methyl-4-chlorophenyl) formamidine, respectively, each of which may be prepared by reacting the appropriate aniline of formula (V) with the appropriate formamide (VI) according to the method of Belgian Pat. No. 760,141; there is obtained N-ethyl-N-(trichloromethylthio)-N'-(2-methyl-4-chlorophenyl) formamidine; N-n-propyl-N-(trichloromethylthio)-N'-(2-methyl-4-chlorophenyl) formamidine; and N-isopropyl-N-(trichloromethylthio)-N'-(2-methyl-4-chlorophenyl) formamidine, respectively.

EXAMPLE 9

N-Methyl-N-(p-tolylthio)-N'-(2-methyl-4-chlorophenyl) formamidine

To 4.56 gms. (0.025 mole) of N-methyl-N'-(2-methyl-4-chlorophenyl) formamidine in 100 ml. tetrahydrofuran is added 2.55 gms. (0.025 mole) of triethylamine. The mixture is cooled in an ice bath and 3.97 gms. (0.025 mole) of p-toluenesulfenyl chloride is added with stirring. The reaction mixture is then stirred at room temperature for ½ hour, filtered and the filtrate stripped of solvent to yield 7.0 gms. (92% of theory) of N-methyl-N-(p-tolylthio)-N'-(2-methyl-4-chlorophenyl) formamidine in the form of white crystals. Recrystallized from Skellysolve F, an analytical sample is obtained; m.p. 49° C. – 50.5° C.

EXAMPLE 10

N-Methyl-N-(methylthio)-N'-2,4-xylyl formamidine

To 3.24 gms. (0.02 mole) of N-methyl-N'-2,4-xylyl formamidine in 100 ml. tetrahydrofuran there is added 2.02 gms. (0.02 mole) of triethylamine. The mixture is cooled in an ice bath and 1.65 gms. (0.02 mole) of methanesulfenyl chloride is added with stirring. The reaction mixture is then stirred at room temperature for ½ hour, filtered and the filtrate stripped of solvent. The oil obtained is purified by a quick filtration through 10 gms. of silica gel using ethyl acetate as an elutent to give 2.0 gms. (48.5% of theory) of N-methyl-N-(methylthio)-N'-2,4-xylyl formamidine in the form of a light amber oil.

Analysis: Calc'd. for $C_{11}H_{16}N_2S$ (percent); C, 63.42; H, 7.74; N, 13.45. Found (percent); C, 63.47; H, 7.69; N, 12.85.

Similarly, following the above procedure but replacing the N-methyl-N'-2,4-xylyl formamidine as used therein with an equal molar proportion of N-ethyl-N'-2,4-xylyl formamidine; N-n-propyl-N'-2,4-xylyl formamidine; and N-isopropyl-N'-2,4-xylyl formamidine, respectively, all of which are prepared by reaction of the appropriate aniline of formula (V) with an appropriate formamide (VI) according to the method of Belgian Pat. No. 760,141; there is obtained N-ethyl-N-(methylthio)-N'-2,4-xylyl formamidine; N-n-propyl-N-(methylthio)-N'-2,4-xylyl formamidine; and N-isopropyl-N-(methylthio)-N'-2,4-xylyl formamidine, respectively.

EXAMPLE 11

N-Methyl-N-(methylthio)-N'-(2-methyl-4-chlorophenyl) formamidine

To 3.65 gms. (0.02 mole) of N-methyl-N'-(2-methyl-4-chlorophenyl) formamidine in 100 ml. tetrahydrofuran there is added 2.02 gms. (0.02 mole) of triethylamine. The mixture is cooled in an ice bath and 1.65 gms. (0.02 mole) of methanesulfenyl chloride is added with stirring. The reaction mixture is then stirred at room temperature for ½ hour, filtered and the filtrate stripped of solvent. The oil obtained is purified by filtration through 10 gms. of silica gel using ethyl acetate as an elutent to give 1.8 gms. (39% of theory) of N-methyl-N-(methylthio)-N'-(2-methyl-4-chlorophenyl) formamidine in the form of a light amber oil.

Analysis: Calc'd. for $C_{10}H_{13}ClN_2S$ (percent); C, 52.51; H, 5.73; N, 12.25. Found (percent); C, 52.38; H, 5.84; N, 12.12.

Similarly, following the above procedure but replacing the N-methyl-N'-(2-methyl-4-chlorophenyl) formamidine as used therein with an equal molar proportion of N-ethyl-N'-(2-methyl-4-chlorophenyl) formamidine; N-n-propyl-N'-(2-methyl-4-chlorophenyl) formamidine; and N-isopropyl-N'-(2-methyl-4-chlorophenyl) formamidine, respectively, all of which are prepared by reaction of an appropriate aniline (V) with an appropriate formamide (VI) according to the method of Belgian Pat. No. 760,141; there is obtained N-ethyl-N-(methylthio)-N'-(2-methyl-4-chlorophenyl) formamidine, N-n-propyl-N-(methylthio)-N'-(2-methyl-4-chlorophenyl) formamidine, and N-isopropyl-N-(methylthio)-N'-(2-methyl-4-chlorophenyl) formamidine, respectively.

EXAMPLE 12

N-Methyl-N-(trichloromethylthio)-N'-o-tolyl formamidine

To 1.48 gms. (0.01 mole) of N-methyl-N'-o-tolyl formamidine in 50 ml. tetrahydrofuran there is added 1.01 gms. (0.01 mole) of triethylamine. The mixture is cooled in an ice bath and 1.85 gms. (0.01 mole) of trichloromethanesulfenyl chloride is added with stirring. The reaction mixture is then stirred at room temperature for ½ hour, filtered and the filtrate stripped of solvent. The oil obtained is filtered quickly through 20 gms. of silica gel using benzene as an elutent to give 2.0 gms. (67% of theory) of N-methyl-N-(trichloromethylthio)-N'-o-tolyl formamidine in the form of a yellow oil.

Analysis: Calc'd. for $C_{10}H_{11}Cl_3N_2S$ (percent); C, 40.36; H, 3.73; N, 9.41. Found (percent); C, 40.30; H, 3.74; N, 9.46.

EXAMPLE 13

N-Methyl-N-(4-chlorophenylthio)-N'-2,4-xylyl formamidine

To 3.24 gms. (0.02 mole) of N-methyl-N'-2,4-xylyl formamidine in 100 ml. tetrahydrofuran there is added 2.02 gms. (0.02 mole) of triethylamine. The mixture is cooled in an ice bath and 3.58 gms. (0.02 mole) of 4-chlorophenylsulfenyl chloride is added with stirring. The reaction mixture is stirred at room temperature for ½ hour, filtered and the filtrate stripped of solvent to yield 5.8 gms. (95% of theory) of N-methyl-N-(4-chlorophenylthio)-N'-2,4-xylyl formamidine in the form of a colorless oil.

Analysis: Calc'd. for $C_{16}H_{17}ClN_2S$ (percent); C, 63.04; H, 5.62; N, 9.19. Found (percent); C, 63.20; H, 5.68; N, 9.17.

EXAMPLE 14

N-Methyl-N-(4-chlorophenylthio)-N'-(2-methyl-4-chlorophenyl) formamidine

To 3.65 gms. (0.02 mole) of N-methyl-N'-(2-methyl-4-chlorophenyl) formamidine in 100 ml. tetrahydrofuran is added 2.02 gms. (0.02 mole) of triethylamine. The mixture is cooled in an ice bath and 3.58 gms. (0.02 mole) of 4-chlorophenylsulfenyl chloride is added with stirring. The reaction mixture is stirred at room temperature for ½ hour, filtered and the filtrate stripped of solvent to yield 6.0 gms. (92.5% of theory) of N-methyl-N-(4-chlorophenylthio)-N'-(2-methyl-4-chlorophenyl) formamidine in the form of a colorless oil.

Analysis: Calc'd. for $C_{15}H_{14}Cl_2N_2S$ (percent); C, 55.39; H, 4.34; N, 8.61. Found (percent); C, 55.25; H, 4.47; N, 8.56.

Similarly, repeating the above procedure but replacing the N-methyl-N'-(2-methyl-4-chlorophenyl) formamidine as used therein with an equal molar proportion of each of the following compounds of formula (III):
N-methyl-N'-2-butylphenyl formamidine;
N-methyl-N'-2-bromophenyl formamidine;
N-methyl-N'-2-trifluoromethylphenyl formamidine;
N-methyl-N'-2-methoxyphenyl formamidine;
N-methyl-N'-2-butoxyphenyl formamidine;
N-methyl-N'-2-thiomethylphenyl formamidine;
N-methyl-N'-2-thiobutylphenyl formamidine;
N-methyl-N'-2,3-dimethylphenyl formamidine;

N-methyl-N'-(3-chloro-2-methylphenyl) formamidine;
N-methyl-N'-(3-butoxy-2-chlorophenyl) formamidine;
N-methyl-N'-(2-methyl-3-thiomethylphenyl) formamidine;
N-methyl-N'-(2-butyl-4-trichloromethylphenyl) formamidine;
N-methyl-N'-(4-isopropoxy-2-methylphenyl) formamidine;
N-methyl-N'-(2-ethyl-4-thiomethylphenyl) formamidine;
N-methyl-N'-2,5-dimethylphenyl formamidine;
N-methyl-N'-2,5-diiodophenyl formamidine;
N-methyl-N'-2,5-diethoxyphenyl formamidine;
N-methyl-N'-2,5-ditrichloromethylphenyl formamidine;
N-methyl-N'-2,5-dithiobutylphenyl formamidine;
N-methyl-N'-2,6-dibutylphenyl formamidine;
N-methyl-N'-(6-fluoro-2-methylphenyl) formamidine;
N-methyl-N'-(2-ethyl-6-trifluoromethylphenyl) formamidine;
N-methyl-N'-(6-butoxy-2-methylphenyl) formamidine;
N-methyl-N'-(2-methyl-6-thiopropylphenyl) formamidine;
N-methyl-N'-2,4,6-trimethylphenyl formamidine;
N-methyl-N'-2,3,4,5,6-pentafluorophenyl formamidine;
N-methyl-N'-(2,3-dimethoxy-6-methylphenyl) formamidine;
N-methyl-N'-(2,6-dimethyl-4-trichloromethylphenyl) formamidine;
N-methyl-N'-(3,5-dichloro-2,4,6-trichloromethylphenyl) formamidine; and
N-methyl-N'-(2-methyl-3,5-dithiobutylphenyl) formamidine, all of which may be prepared by reacting N-methylformamide with the appropriate compound of formula (V), supra, according to the method described above; and N-t-butyl-N'-2,4-xylyl formamidine which may be similarly prepared by reacting N-t-butylformamide with 2,4-dimethylaniline, respectively, there is obtained:

N-methyl-N-(4-chlorophenylthio)-N'-2-butylphenyl formamidine;
N-methyl-N-(4-chlorophenylthio)-N'-2-bromophenyl formamidine;
N-methyl-N-(4-clorophenylthio)-N'-2-trifluoromethylphenyl formamidine;
N-methyl-N-(4-chlorophenylthio)-N'-2-methoxyphenyl formamidine;
N-methyl-N-(4-chlorophenylthio)-N'-2-butoxyphenyl formamidine;
N-methyl-N-(4-chlorophenylthio)-N'-2-thiomethylphenyl formamidine;
N-methyl-N-(4-chlorophenylthio)-N'-2-thiobutylphenyl formamidine;
N-methyl-N-(4-chlorophenylthio)-N'-2,3-dimethylphenyl formamidine;
N-methyl-N-(4-chlorophenylthio)-N'-(3-chloro-2-methylphenyl) formamidine;
N-methyl-N-(4-chlorophenylthio)-N'-(3-butoxy-2-chlorophenyl) formamidine;
N-methyl-N-(4-chlorophenylthio)-N'-(2-methyl-3-thiomethylphenyl) formamidine;
N-methyl-N-(4-chlorophenylthio)-N'-(2-butyl-4-trichloromethylphenyl) formamidine;
N-methyl-N-(4-chlorophenylthio)-N'-(4-isopropoxy-2-methylphenyl) formamidine;
N-methyl-N-(4-chlorophenylthio)-N'-(2-ethyl-4-thiomethylphenyl) formamidine;
N-methyl-N-(4-chlorophenylthio)-N'-2,5-dimethylphenyl formamidine;
N-methyl-N-(4-chlorophenylthio)-N'-2,5-diiodophenyl formamidine;
N-methyl-N-(4-chlorophenylthio)-N'-2,5-diethoxyphenyl formamidine;
N-methyl-N-(4-chlorophenylthio)-N'-2,5-trichloromethylphenyl formamidine;
N-methyl-N-(4-chlorophenylthio)-N'-2,5-dithiobutylphenyl formamidine;
N-methyl-N-(4-chlorophenylthio)-N'-2,6-dibutylphenyl formamidine;
N-methyl-N-(4-chlorophenylthio)-N'-(6-fluoro-2-methylphenyl) formamidine;
N-methyl-N-(4-chlorophenylthio)-N'-(2-ethyl-6-trifluoromethylphenyl) formamidine;
N-methyl-N-(4-chlorophenylthio)-N'-(6-butoxy-2-methylphenyl) formamidine;
N-methyl-N-(4-chlorophenylthio)-N'-(2-methyl-6-thiopropylphenyl) formamidine;
N-methyl-N-(4-chlorophenylthio)-N'-2,4,6-trimethylphenyl formamidine;
N-methyl-N-(4-chlorophenylthio)-N'-2,3,4,5,6-pentafluorophenyl formamidine;
N-methyl-N-(4-chlorophenylthio)-N'-(2,3-dimethoxy-6-methylphenyl) formamidine;
N-methyl-N-(4-chlorophenylthio)-N'-(2,6-dimethyl-4-trichloromethylphenyl) formamidine;
N-methyl-N-(4-chlorophenylthio)-N'-(3,5-dichloro-2,4,6-trichloromethylphenyl) formamidine;
N-methyl-N-(4-chlorophenylthio)-N'-(2-methyl-3,5-dithiobutylphenyl) formamidine; and
N-t-butyl-N-(4-chlorophenylthio)-N'-2,4-dimethylphenyl formamidine, respectively.

EXAMPLE 15

N-methyl-N-(trichloromethylthio)-N'-2,4-xylyl formamidine hydrochloride

An appropriate reaction vessel is charged with 30 ml. of ether saturated with dissolved hydrogen chloride. The solution is cooled to circa 10° C. and 4.0 gms. of N-methyl-N-(trichloromethylthio)-N'-2,4-xylyl formamidine (Example 6, supra.) in 10 ml. of diethyl ether is added dropwise with stirring. There appears in the reaction mixture a white precipitate. After no more precipitate appears, the mixture is filtered, the precipitate washed with ether and dried to give 3.2 gms. of N-methyl-N-(trichloromethylthio)-N'-2,4-xylyl formamidine hydrochloride in the form of a white solid, m.p. 82° C – 83° C.

Similarly, following the above procedure, but replacing the N-methyl-N-(trichloromethylthio)-2,4-xylyl formamidine as used therein with any other compound (I), the corresponding hydrochloride salt is obtained.

The following example illustrates a composition of the invention.

EXAMPLE 16

A dispersible powder formulation is obtained by blending and milling 327 lbs. of Georgia Clay, 4.5 lbs. of isooctylphenoxy ethanol (Triton X-100) as a wetting agent, 9 lbs. of a polymerized sodium salt of substituted benzoid long-chain sulfonic acid (Daxad 27) as a dispersing agent, and 113 lbs. of N-methyl-N-(p-tolylthio)-N'-(2-methyl-4-chlorophenyl) formamidine (Example 9, supra.). The resulting formulation has the following percentage composition (parts herein are by weight unless otherwise specified).

| | |
|---|---|
| N-methyl-N-(p-tolylthio)-N'-(2-methyl-4-chlorophenyl) formamidine | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to invertebrate pests, plants or other invertebrate pest habitats or invertebrate pest foods to kill such pests.

Similarly, replacing the N-methyl-N-(p-tolylthio)-N'-(2-methyl-4-chlorophenyl) formamidine as used in the above example with an equal proportion of any other compound of the formula (I) as prepared in Examples 1–15, supra., a pesticidal composition is obtained which will kill and control invertebrate pests.

I claim:

1. An arthropodicidal composition which comprises a pesticidally acceptable carrier, and an effective amount of a compound selected from the group consisting of those of formula:

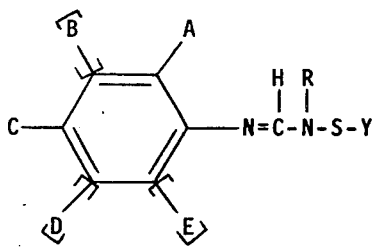

and the acid addition salts thereof wherein A is a member selected from the group consisting of halogen, lower alkyl, halogen-substituted lower alkyl, lower alkoxy and lower thioalkyl; C, is selected from the group consisting of hydrogen and a member of group A as defined above; R represents lower alkyl and Y is selected from the group consisting of lower alkyl, halogen substituted lower alkyl, phenyl, halogen substituted phenyl, lower alkyl-substituted phenyl and lower alkoxy-substituted phenyl.

2. A composition according to claim 1 wherein said compound is present in a concentration of from 30 to about 6000 parts per million.

3. A process for killing arthropod pests which comprises applying to their situs an effective amount of a compound selected from the group consisting of those having the formula:

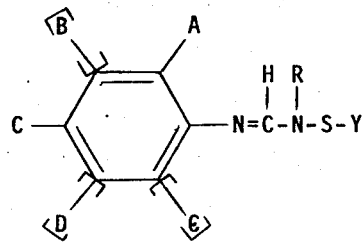

and the acid addition salts thereof wherein A is a member selected from the group consisting of halogen, lower alkyl, halogen-substituted lower alkyl, lower alkoxy and lower thioalkyl; C, is selected from the group consisting of hydrogen and a member of group A as defined above; R represents lower alkyl and Y is selected from the group consisting of lower alkyl, halogen substituted lower alkyl, phenyl, halogen substituted phenyl, lower alkyl-substituted phenyl and lower alkoxy-substituted phenyl.

4. A process according to claim 3 wherein said compound is applied in combination with a pesticidally acceptable carrier.

5. A process according to claim 3 wherein application is to said invertebrate pests in the oval stage.

6. A process for killing Acarina which comprises applying to their situs an effective amount of a compound selected from the group consisting of those having the formula:

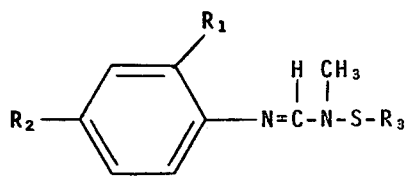

and the acid addition salts thereof, wherein $R_1$ is lower alkyl, $R_2$ is selected from the group consisting of hydrogen, halogen and lower alkyl and $R_3$ is selected from the group consisting of lower alkyl, phenyl, halogen-substituted phenyl, lower alkyl-substituted phenyl, lower alkoxy-substituted phenyl and halogen-substituted lower alkyl.

7. A process according to claim 6 wherein said compound is applied in combination with a pesticidally acceptable carrier.

8. A process according to claim 6 wherein application is to said Acarina in the oval stage.

9. The process according to claim 3 wherein A and C are lower alkyl, R is methyl, and Y is phenyl or lower alkyl-substituted phenyl.

10. A process according to claim 9 wherein the compound is N-methyl-N-(phenylthio)-N'-2,4-xylyl formamidine.

11. A process according to claim 9 wherein the compound is N-methyl-N-(p-tolylthio)-N'-2,4-xylyl formamidine.

* * * * *